United States Patent
Chevalier

(10) Patent No.: US 11,766,278 B2
(45) Date of Patent: Sep. 26, 2023

(54) IMPLANTABLE DISTRACTION DEVICE

(71) Applicant: NuVasive, Inc., San Diego, CA (US)

(72) Inventor: Éric Chevalier, Arras (FR)

(73) Assignee: NuVasive, Inc., San Diego, CA (US)

(*) Notice: Subject to any disclaimer, the term of this patent is extended or adjusted under 35 U.S.C. 154(b) by 0 days.

(21) Appl. No.: 16/768,670

(22) PCT Filed: Nov. 30, 2018

(86) PCT No.: PCT/EP2018/083216
§ 371 (c)(1),
(2) Date: May 30, 2020

(87) PCT Pub. No.: WO2019/106183
PCT Pub. Date: Jun. 6, 2019

(65) Prior Publication Data
US 2021/0186563 A1    Jun. 24, 2021

Related U.S. Application Data

(63) Continuation of application No. 15/947,495, filed on Apr. 6, 2018, now Pat. No. 11,376,043.

(30) Foreign Application Priority Data

Nov. 30, 2017  (EP) .................................... 17306662

(51) Int. Cl.
*A61B 17/66* (2006.01)
*G01H 11/08* (2006.01)
(Continued)

(52) U.S. Cl.
CPC .......... *A61B 17/663* (2013.01); *A61B 5/0051* (2013.01); *A61B 5/4504* (2013.01);
(Continued)

(58) Field of Classification Search
CPC . A61B 17/66; A61B 17/663; A61B 2017/681; A61B 5/0051; A61B 17/666; A61B 17/60; G01H 11/08
See application file for complete search history.

(56) References Cited

U.S. PATENT DOCUMENTS 3,976,060 A   8/1976 Hildebrandt et al.
5,263,955 A   11/1993 Baumgart et al.
(Continued)

FOREIGN PATENT DOCUMENTS

GB    2156983 A    10/1985

OTHER PUBLICATIONS

International Search Report for PCT/EP18/83216 (dated Feb. 18, 2019), 2 pages.
(Continued)

*Primary Examiner* — Eduardo C Robert
*Assistant Examiner* — Christina Negrellirodriguez
(74) *Attorney, Agent, or Firm* — Hoffman Warnick LLC

(57) ABSTRACT

The present invention relates to an implantable bone distraction device (1) for distracting osteotomically separated bone sections (2, 2'), said implantable distraction device (1) comprising a first block (3), a second block (3'), and an actuator (4) including means for adjusting the space between the two blocks, enabling distraction between the first bone section (2) and the second bone section (2'). The implantable bone distraction device (1) further comprises at least one vibration sensor (6) arranged in an area located between the first block (3) and the second block (3') and oriented in order to measure a vibration response of a medium comprising the implantable bone distraction device (1).

18 Claims, 2 Drawing Sheets

(51) Int. Cl.
  *A61B 5/00*  (2006.01)
  *A61B 17/68*  (2006.01)

(52) U.S. Cl.
  CPC ............ *A61B 17/66* (2013.01); *G01H 11/08* (2013.01); *A61B 5/0031* (2013.01); *A61B 5/6847* (2013.01); *A61B 2017/681* (2013.01); *A61B 2562/0219* (2013.01)

(56) References Cited

U.S. PATENT DOCUMENTS

| | | |
|---|---|---|
| 5,334,202 A | 8/1994 | Carter |
| 5,364,396 A | 11/1994 | Robinson et al. |
| 5,415,660 A | 5/1995 | Campbell et al. |
| 5,704,938 A | 1/1998 | Staehlin et al. |
| 5,782,752 A | 7/1998 | Lichtman et al. |
| 5,935,057 A | 8/1999 | Lichtman et al. |
| 5,961,553 A | 10/1999 | Coty et al. |
| 6,245,075 B1 | 6/2001 | Betz et al. |
| 6,383,185 B1 | 5/2002 | Baumgart |
| 6,524,313 B1 | 2/2003 | Fassier et al. |
| 6,730,087 B1 | 5/2004 | Butsch |
| 6,849,076 B2 | 2/2005 | Blunn et al. |
| 7,063,706 B2 | 6/2006 | Wittenstein |
| 7,530,981 B2 | 5/2009 | Kutsenko |
| 7,666,184 B2 | 2/2010 | Stauch |
| 7,753,915 B1 | 7/2010 | Eksler et al. |
| 8,137,349 B2 | 5/2012 | Soubeiran |
| 8,252,063 B2 | 8/2012 | Stauch |
| 8,449,543 B2 | 5/2013 | Pool et al. |
| 8,715,282 B2 | 5/2014 | Pool |
| 8,734,488 B2 | 5/2014 | Pool et al. |
| 8,777,947 B2 | 7/2014 | Zahrly et al. |
| 8,852,187 B2 | 10/2014 | Pool et al. |
| 9,044,281 B2 | 6/2015 | Pool et al. |
| 9,113,967 B2 | 8/2015 | Soubeiran |
| 9,138,266 B2 | 9/2015 | Stauch |
| 9,179,938 B2 | 11/2015 | Pool et al. |
| 9,186,183 B2 | 11/2015 | Pool et al. |
| 9,393,117 B2 | 7/2016 | Pool |
| 9,393,119 B2 | 7/2016 | Pool et al. |
| 9,308,089 B2 | 8/2016 | Vicatos et al. |
| 9,421,046 B2 | 8/2016 | Pool et al. |
| 9,615,864 B2 | 4/2017 | Kuiken |
| 9,636,153 B2 | 5/2017 | Stauch |
| 9,757,159 B2 | 9/2017 | Pool et al. |
| 9,770,274 B2 | 9/2017 | Pool et al. |
| 9,943,345 B2 * | 4/2018 | Nill .................... A61B 17/7016 |
| 9,962,199 B2 | 5/2018 | Forsell |
| 10,064,664 B2 | 9/2018 | Forsell |
| 10,105,167 B2 | 10/2018 | Pool et al. |
| 10,251,676 B2 | 4/2019 | Brunner et al. |
| 10,271,885 B2 | 4/2019 | Quach et al. |
| 10,314,619 B2 * | 6/2019 | Roschak ............ A61B 17/7016 |
| 10,405,891 B2 | 9/2019 | Pool et al. |
| 10,617,453 B2 | 4/2020 | Beckett et al. |
| 10,646,262 B2 | 5/2020 | Pool |
| 11,376,043 B2 * | 7/2022 | Chevalier ............ A61B 5/4504 |
| 2006/0235424 A1 | 10/2006 | Vitale et al. |
| 2007/0173837 A1 * | 7/2007 | Chan .................... A61B 17/66 606/63 |
| 2009/0112207 A1 * | 4/2009 | Walker ............... A61B 17/8004 600/12 |
| 2009/0192514 A1 | 7/2009 | Feinberg et al. |
| 2010/0152621 A1 * | 6/2010 | Janna .................. A61B 5/4504 600/595 |
| 2010/0249787 A1 * | 9/2010 | Roche .................. A61B 5/4509 600/587 |
| 2015/0025587 A1 * | 1/2015 | Kim .................... A61B 17/663 606/282 |
| 2015/0250505 A1 | 9/2015 | Ross et al. |
| 2018/0317980 A1 | 11/2018 | Forsell |
| 2019/0015138 A1 | 1/2019 | Schwardt et al. |
| 2019/0133650 A1 | 5/2019 | Haaja et al. |
| 2019/0175231 A1 | 6/2019 | Forsell |
| 2019/0201067 A1 | 7/2019 | Quach et al. |
| 2019/0254712 A1 | 8/2019 | Roschak et al. |
| 2019/0336183 A1 | 11/2019 | Farley et al. |
| 2019/0350627 A1 | 11/2019 | Pool et al. |
| 2020/0022741 A1 | 1/2020 | Janda et al. |

OTHER PUBLICATIONS

Written Opinion for PCT/EP18/83216 (dated Feb. 25, 2019), 6 pages.
Extended European Seach Report for corresponding EP17306662.2 (dated May 18, 2018), 8 pages.
Translation of Office Action (Notice of Reasons for Rejection) for Japanese Application No. 2020-547306 dated Jan. 10, 2023, 7 pages.
Cited Reference 2 in Japanese Office Action—Success in Development of "Bone Diagnostic Equipment by Measuring Natural Vibration Frequency," Japan Science and Technology Corporation Report, No. 115, Japan, dated Aug. 27, 1999; according to translation of Japanese Office Action, this reference is only published in Japanese; we have included a Google Translate version of the abstract, 5 pages.

* cited by examiner

IMPLANTABLE DISTRACTION DEVICE

PRIORITY CLAIM

This application is a national stage entry of PCT/EP2018/083216, filed Nov. 30, 2018, which claims priority to U.S. patent application Ser. No. 15/947,495, filed Apr. 6, 2018, and European Patent Application Serial No. 17306662.2, filed Nov. 30, 2017, the entire contents of each of which are incorporated herein by reference and relied upon.

FIELD OF INVENTION

The present invention pertains to the field of implantable bone distraction devices.

BACKGROUND OF INVENTION

Distraction osteogenesis is a technique which has been used to grow new bone in patients with a variety of defects. For example, limb lengthening is a technique in which the length of a bone (for example a femur or a tibia) may be increased. By creating a corticotomy, or osteotomy, in the bone, which is a cut through the bone, the two resulting bone sections may be moved apart at a particular rate, such as one millimeter per day, allowing new bone to regenerate between the two sections as they move apart. This technique of limb lengthening is used in cases where one limb is longer than the other, such as in a patient whose prior bone break did not heal correctly, or in a patient whose growth plate was diseased or damaged prior to maturity. In some patients, stature lengthening is desired, and is achieved by lengthening both femurs and/or both tibia to increase the patient's height.

The prior art includes the U.S. Pat. No. 5,364,396 which discloses an implantable bone distraction device and a method associated. This implantable bone device comprises two blocks, each fixed to a separated bone section and linked together to a rotatable drive rod and a drive rod actuator. The actuation of the drive rod actuator leads to a rotation of the rotatable drive rod which moves apart the two blocks.

However, the speed or the rate of the move of the two resulting bone sections is critical. Indeed, the osteotomy results in a gap between the two separated bone sections. The callus is used herein to describe the heterogeneous tissue involved in the intermediate stage of bone formation or bone healing in the gap between the two separated bone sections.

If the rate is too fast, said callus may be split and no bone healing process will occur. If the rate is too slow, the bone healing process may be too developed to move apart the two bone sections and a new osteotomy will be needed.

Therefore, the present invention is intended to provide an implantable bone distraction device and a medical monitoring device to continuously or semi-continuously monitor and identify the bone healing process between separated bone sections.

SUMMARY

This invention thus relates, in a first aspect, to an implantable bone distraction device for distracting osteotomically separated bone sections, said implantable distraction device comprising:
- a first block for implantation and attachment to a first bone section, said first block defining a first chamber bore;
- a second block for implantation and attachment to a second bone section separated from the first bone section by an osteotomy, said second block defining a second chamber bore;
- an actuator including means for adjusting the space between the first block and the second block when activated, enabling distraction between the first bone section and the second bone section;
- at least one vibration sensor arranged in an area located between the first block and the second block and oriented in order to measure a vibration response of a medium comprising the implantable bone distraction device.

In one embodiment, the implantable distraction device comprises a drive rod having a first end received in said first chamber bore and a second end, opposite from said first end, received in said second chamber bore; said drive rod being able to adjust the space between the first block and the second block.

In one embodiment, said at least one vibration sensor is oriented in order to measure a vibration response of a medium comprising the implantable bone distraction device in the direction of the drive rod.

An advantage of the device of the invention is its ability to measure criteria of the formation of the callus in order to give an indicator to an operator or a doctor, said indicator being representative of the state of the fusion. The arrangement of the sensor contributes to generate a relevant indicator.

According to one embodiment, the at least one vibration sensor is a piezoelectric element or an accelerometer. According to one embodiment, the at least on vibration sensor is arranged to measure a vibration response corresponding to mechanical vibrations.

According to one embodiment, the medium further comprises the first separated bone section and the second separated bone section.

According to one embodiment, the at least one vibration sensor is arranged to measure an evolution of the vibration response of the medium, allowing monitoring of the evolution of the bone fusion process.

According to one embodiment the implantable bone distraction device comprises a drive rod actuator cooperating with said drive rod to adjust the space between the first block and second block when activated, enabling distraction between the first bone section and the second bone section.

According to one embodiment, the first chamber bore is a drive chamber bore; the second chamber bore is a threaded bore; the second end of the drive rod is a threaded end threadably received in the threaded bore of the second block; and the actuator cooperates with said drive rod to rotate said drive rod; said drive rod being able to adjust the space between the first block and the second block by rotation.

According to one embodiment, the implantable bone distraction device comprises at least one vibration sensor oriented so as to measure a vibration response of the medium in the direction of the drive rod.

According to one embodiment, the implantable bone distraction device comprises at least two vibration sensors, including a first vibration sensor for measuring a vibration response of the medium in the longitudinal direction of the drive rod and a second vibration sensor for measuring a vibration response of the medium in a direction perpendicular to the longitudinal direction of the drive rod.

According to one embodiment, the implantable bone distraction device further comprises a wireless interface for transmitting data measured by the at least one vibration sensor.

According to one embodiment, the implantable bone distraction device does not comprise a vibration excitation transducer.

According to one embodiment, the implantable bone distraction device further comprises a memory to store data measured by the at least one vibration sensor.

In a second aspect, the present invention relates to a medical monitoring device comprising:
- a receiver for receiving data from an implantable bone distraction device, corresponding to a mechanical vibration response of a medium comprising the implantable bone distraction device, as measured by at least one vibration sensor;
- a calculator for computing, from the data received by the receiver, a distraction indicator through at least the steps of:
  - determining at least one vibration pattern of said medium from the vibration response measured by the at least one vibration sensor;
  - analyzing the evolution of a first value of the at least one vibration pattern of said medium, determined from the measured vibration response measured by the at least one vibration sensor during a first period;
  - generating a distraction indicator as a function of the first value.

According to one embodiment, the step of generating a distraction indicator is executed when the first value exceeds a predefined threshold.

According to one embodiment, the medical monitoring device comprises:
- a receiver for receiving data from an implantable bone distraction device, corresponding to a mechanical vibration response of a medium comprising the implantable bone distraction device, as measured by at least one vibration sensor;
- a calculator for computing, from the data received by the receiver, a distraction indicator through at least the steps of:
  - determining at least one vibration pattern of said medium from the vibration response measured by the at least one vibration sensor;
  - analyzing the evolution of a first value of the at least one vibration pattern of said medium, determined from the measured vibration response measured by the at least one vibration sensor during a first period;
  - analyzing the evolution of a second value of the at least one vibration pattern of said medium, determined from the measured vibration response measured by the at least one vibration sensor during a second period;
  - performing a comparison between the first value and the second value;
  - generating a distraction indicator as a function of said comparison.

According to one embodiment, the step of generating a distraction indicator is executed when said comparison exceeds a predefined threshold.

According to one embodiment, the at least one vibration pattern is a resonant frequency of the medium.

According to one embodiment, the at least one vibration pattern is a function of the damping factor.

The processing steps of the signal contribute to generate a relevant indicator, for example by determining a relevant pattern and achieving correlation functions with some relevant values and for instance by comparing the different values of said pattern in a predefined duration.

According to one embodiment, the medical monitoring device further comprises a transmitter for transmitting, to the implantable bone distraction device, instructions for providing a distraction when a distraction indicator is generated by the calculator.

According to one embodiment, the mechanical vibration response of the medium measured by the at least one vibration sensor allows monitoring of the evolution of the bone fusion process.

In a third aspect, the present invention relates to a medical system comprising an implantable bone distraction device according to the first aspect of present invention and a medical monitoring device according to the second aspect of present invention, wherein said medical system comprises an interface which activates the transmission of vibration data from the implantable bone distraction device, to be received by the medical monitoring device, wherein the vibration data correspond to a mechanical vibration response of a medium comprising the implantable bone distraction device, as measured by at least one vibration sensor.

The implantable bone distraction device and the medical monitoring device cooperate to produce a combined technical effect so as to improve the indicator related to the bone fusion process. The specific arrangement of the bone distraction device, and in particular of the at least one vibration sensor, and the steps performed by the calculator allowing the extraction of the at least one vibration pattern according to the invention, when used in combination, allow the medical system to be particularly efficient.

According to one embodiment, the implantable bone distraction device comprises actuation means for actuating the actuator, and the medical monitoring device comprises a transmitter connected to said actuation means for automatically activating the actuator when a distraction indicator is generated.

In a fourth aspect, the present invention relates to a method for generating a distraction indicator, comprising:
- receiving data from an implantable bone distraction device, corresponding to a mechanical vibration response of a medium comprising the implantable bone distraction device, as measured by at least one vibration sensor;
- computing, from the received data, a distraction indicator through at least the steps of:
  - determining at least one vibration pattern of said medium from the vibration response measured by the at least one vibration sensor;
  - analyzing the evolution of a first value of the at least one vibration pattern of said medium, determined from the measured vibration response measured by the at least one vibration sensor during a first period;
  - generating a distraction indicator as a function of said first value.

According to one embodiment, the step of generating a distraction indicator is executed when the first value exceeds a predefined threshold.

According to one embodiment, the method for generating a distraction indicator comprises:
- receiving data from an implantable bone distraction device, corresponding to a mechanical vibration response of a medium comprising the implantable bone distraction device, as measured by at least one vibration sensor;

computing, from the received data, a distraction indicator through at least the steps of:
  determining at least one vibration pattern of said medium from the vibration response measured by the at least one vibration sensor;
  analyzing the evolution of a first value of the at least one vibration pattern of said medium, determined from the measured vibration response measured by the at least one vibration sensor during a first period;
  analyzing the evolution of a second value of the at least one vibration pattern of said medium, determined from the measured vibration response measured by the at least one vibration sensor during a second period;
  performing a comparison between the first value and the second value;
  generating a distraction indicator as a function of said comparison.

According to one embodiment, the step of generating a distraction indicator is executed when said comparison exceeds a predefined threshold.

According to one embodiment, the method further comprises a step of transmitting, to the implantable bone distraction device, instructions for providing a distraction when a distraction indicator is generated.

According to one embodiment, said method further comprises a step of adjusting the space between two separated bone sections by increasing or reducing said space of a predetermined pitch when a distraction indicator is generated.

DEFINITIONS

In the present invention, the following terms have the following meanings:
  "Block": refers to a part configured to be attached to a bone section.
  "Resonant frequency": refers to the frequency at which the response amplitude is a relative maximum.
  "Peak": refers to a frequency or a narrow range of frequencies for which the response amplitude is a relative maximum.
  "Vibration response": refers to an amplitude of a movement of an object or a system on its own until it returns to its resting state.
  "Young's modulus": refers to the elastic modulus, measuring the stiffness of a solid material.
  "Vibration pattern": refers to a characteristic of a vibration data, said vibration pattern may be extracted through a vibration signal or a vibration spectrum, or any other signal processing.
  "Bone fusion process": refers to the process of formation of a distraction callus between two separated bone sections or bone regeneration between two bone sections.

DETAILED DESCRIPTION

The first aspect of the present invention relates to an implantable bone distraction device for distracting osteotomically separated bone sections, comprising a vibration sensor to monitor the bone healing process between the two separated bone sections.

Figure 1:
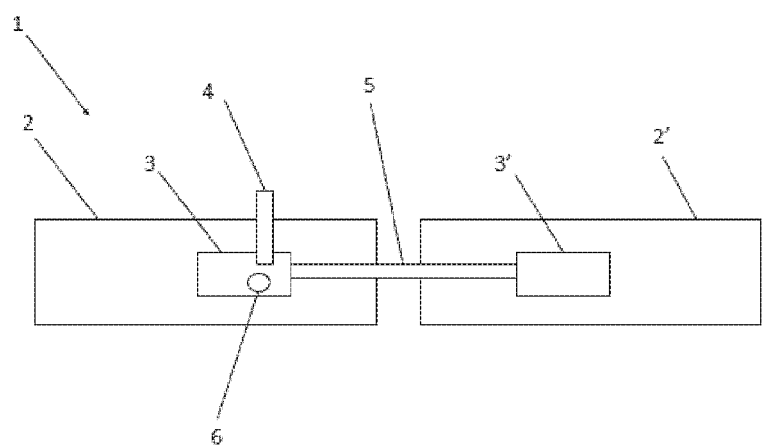
FIG. 1 is a front view of an implantable bone distraction device according to an embodiment mounted on two separated bone sections.

As illustrated in FIG. 1, the implantable bone distraction device 1 comprises a first block 3 for implantation and attachment to a first bone section 2, said first block 3 defining a first chamber bore. The implantable bone distraction device 1 comprises a second block 3' for implantation and attachment to a second bone section 2' separated from the first bone section 2 by an osteotomy, said second block 3' defining a second chamber bore. In one embodiment, the implantable bone distraction device 1 comprises a drive rod 5 having a first end received in said first chamber bore and a second end, opposite from said first end, received in said second chamber bore; said drive rod 5 being able to adjust the space between the first block 3 and the second block 3'.

The implantable bone distraction device 1 further comprises an actuator to adjust the space between the first block 3 and the second block 3' when activated, enabling distraction between the first bone section 2 and the second bone section 2'.

In one embodiment, the actuator is a drive rod actuator 4 cooperating with said drive rod 5 to adjust the space between the first block 3 and the second block 3' when activated, enabling distraction between the first bone section 2 and the second bone section 2'.

The implantable bone distraction device 1 further comprises at least one vibration sensor 6 arranged in an area located between the first block 3 and the second block 3' and oriented in order to measure a vibration response of a medium comprising the implantable bone distraction device 1. In one embodiment, said medium further comprises the first and second bone sections 2, 2'. In one embodiment, the medium further comprises the callus located in the gap between the two separated bone sections. In one embodiment, the medium further comprises the environment of the implantable bone distraction device. In one embodiment, the medium further comprises surrounding tissues of the implantable bone distraction device such as the adjacent bones, muscles, ligaments.

In one embodiment, the vibration sensor 6 is arranged, located and oriented to measure a vibration response which may evolve with the formation of the callus.

Figure 2:
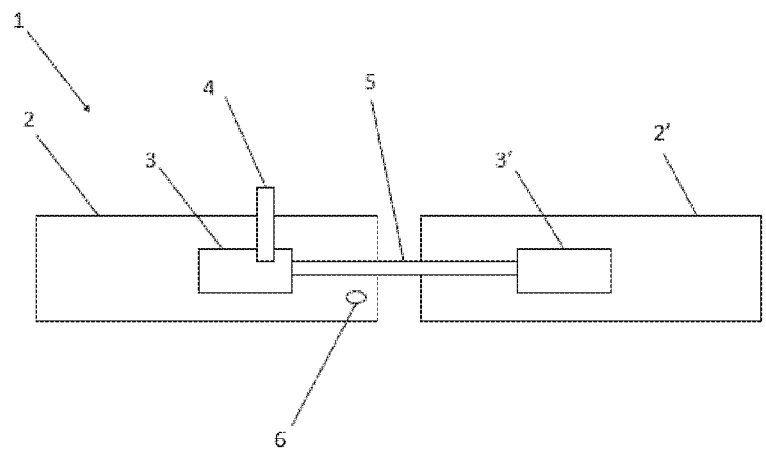
FIG. 2 is a front view of an implantable bone distraction device according to an embodiment mounted on two separated bone sections, the vibration sensor being arranged on one of the separated bone section.
Figure 5:
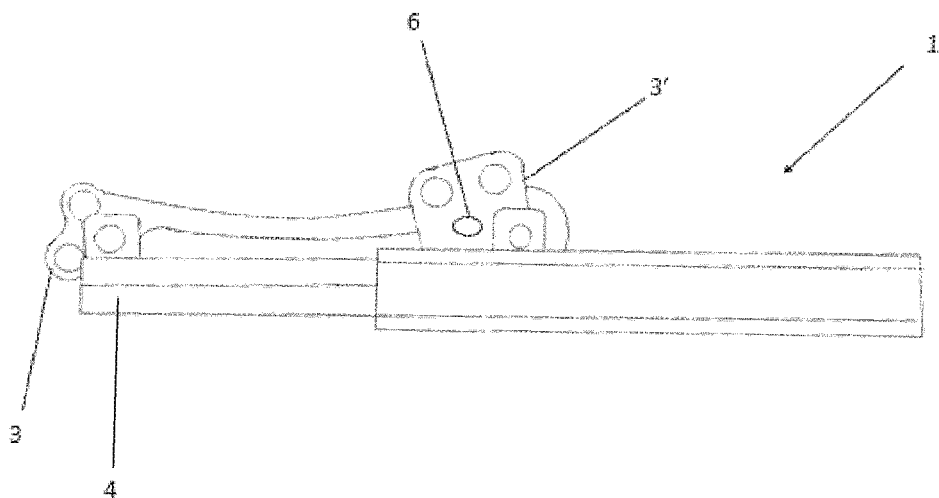
FIG. 5 is a side view of an implantable bone distraction device according to an embodiment integrating a wirelessly powered actuator, and one vibration sensor.

In one embodiment, the vibration sensor 6 is located as close as possible to the callus. In one embodiment, the vibration sensor 6 is located on the implantable bone distraction device 1. In one embodiment, the vibration sensor 6 is located on the first block 3 or on the second block 3' as illustrated in FIG. 1. In one embodiment, the vibration sensor 6 is located on the drive rod 5 or on the drive rod actuator 4. In one embodiment, the vibration sensor is transversally aligned, along the longitudinal direction of the drive rod 5, with the first block 3 or with the second block 3' as illustrated in FIG. 5. In another embodiment as illustrated in FIG. 2, the vibration sensor 6 is configured to be located on the first bone section 2 or on the second bone section 2'.

In one embodiment, said vibration sensor is oriented in order to measure a vibration response of a medium comprising the implantable bone distraction device in the direction of the drive rod.

In one embodiment, the drive rod is a longitudinal element extending along a longitudinal direction in the axis of the first and second blocks. In one embodiment, the vibration sensor 6 is oriented to measure mechanical vibrations in the longitudinal direction of the drive rod 5. In one embodiment, the vibration sensor is oriented to measure mechanical vibrations in a direction perpendicular to the longitudinal direction of the drive rod.

Figure 4:
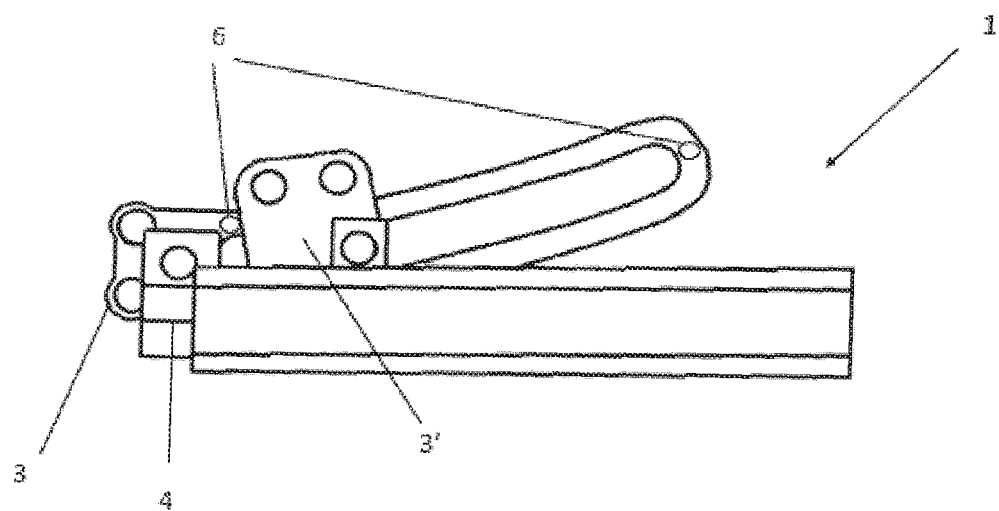
FIG. 4 is a side view of an implantable bone distraction device according to an embodiment integrating a wirelessly powered actuator, and two vibration sensors.

According to one embodiment illustrated in FIG. 4, the first block 3 comprises a longitudinal groove and the second block 3' is able to move along said groove to increase the space between the first and second block, as it can be seen in FIG. 5.

According to one embodiment, the implantable bone distraction device 1 comprises at least two vibration sensors 6: a first vibration sensor for measuring the mechanical vibrations in the longitudinal direction of the drive rod 5 and a second vibration sensor for measuring the mechanical vibrations in a direction perpendicular to the longitudinal direction of the drive rod 5. According to another embodiment, the implantable bone distraction device 1 comprises at least three vibration sensors 6: a first vibration sensor for measuring the mechanical vibrations in the longitudinal direction of the drive rod 5 and a second and a third vibrations sensor for measuring the mechanical vibrations in the two orthogonal directions to the longitudinal direction of the drive rod.

Figure 3:
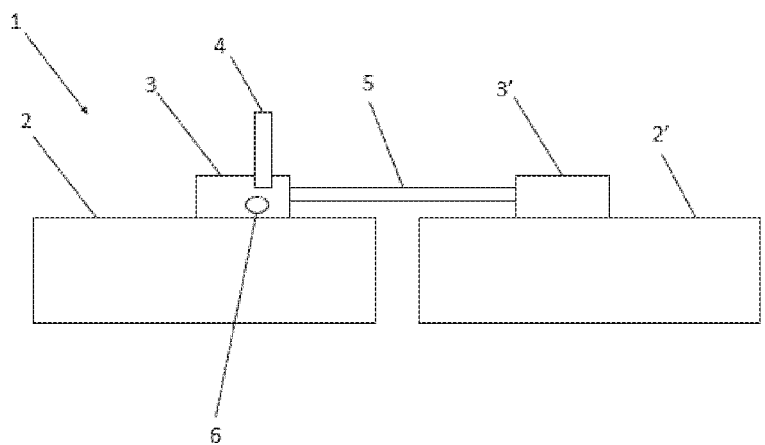
FIG. 3 is a side view of an implantable bone distraction device according to an embodiment mounted on two separated bone sections.

In one embodiment illustrated in FIG. 3, the implantable bone distraction device 1 comprises:
- a first block 3 for implantation and attachment to a first bone section 2, said first block 3 defining a drive chamber bore;
- a second block 3' for implantation and attachment to a second bone section 2' separated from the first bone section 2 by an osteotomy, said second block 3' defining a threaded bore;
- a rotatable drive rod 5 having a first drive end received in said drive chamber bore and a second threaded end, opposite to said first drive end, received in said threaded bore;
- an actuator located is said drive chamber bore cooperating with said first drive end to rotate said first drive end and to adjust the space between the first and second block when activated, enabling distraction between the first and second bone sections.

In one embodiment, the actuator is a drive rod actuator.

In one embodiment, the drive rod actuator includes a distraction screw. The distraction screw cooperates with the drive rod 5 to rotate said drive rod so that the inherent depth to which the threaded distal end of the drive rod is threadably received within said threaded bore can be adjusted. This adjustment makes it possible to adjust the spacing between the first block and the second block, which enables distraction between the first and second bone sections. In this way, bone growth therebetween can be enhanced. In this embodiment, the operator, by screwing the drive rod actuator 4, can control the space between the first block 3 and the second block 3'.

In one embodiment, the at least one vibration sensor 6 continuously or semi-continuously records the vibration response of the medium during a predetermined time. According to one embodiment, the at least one vibration sensor 6 is arranged to measure a vibration response corresponding to mechanical vibrations. According to one embodiment, the at least one vibration sensor 6 is configured to measure a vibration frequency value and/or a vibration amplitude value of said medium. According to one embodiment, the at least one vibration sensor 6 is placed on the first block, on the second block, on the drive rod actuator and/or on the rotatable drive rod.

According to one preferred embodiment, the at least one vibration sensor is a piezoelectric element. The piezoelectric vibration sensor, when exposed to a mechanical stress or a deformation, is able to provide an electric field. The current provided by the piezoelectric element is a function of the intensity of the deformation (or stress). A piezoelectric element is able to measure the amplitude and the frequency of the vibrations.

According to one preferred embodiment, the at least one vibration sensor 6 is an accelerometer element. The said accelerometer is an electromechanical device that may measure both static (gravity) and dynamic (motion or vibration) accelerations.

According to one embodiment, the signal generated by the at least one vibration sensor 6 makes it possible to obtain a frequency spectrum. In one embodiment, the signal generated by the at least one vibration sensor 11 is transformed by a Fourier transform or a wavelet transform to obtain a frequency spectrum.

Indeed, the vibration sensor 6 is able to create an electric charge in response to applied mechanical stress. When a vibration occurs, said vibration sensor measures the vibration response of the medium.

The advantage of this solution is due to the evolution of the callus. Indeed, the stiffness of the callus evolves with the bone fusion process. Furthermore, the evolution of the stiffness of the callus will modify the vibration response of the medium. Then, the evolution of the bone fusion process can be monitored, thereby enabling the generation of an information to an operator. In this way, the operator can control the speed of the distraction between the first and second bone sections as a function of the osteogenesis.

According to one embodiment, the at least one vibration sensor is configured to measure a vibration response of said medium at a frequency ranging of from 20 Hz to 10000 Hz, preferably from 30 Hz to 7000 Hz, more preferably from 40 Hz to 5000 Hz.

According to one embodiment, said implantable bone distraction device 1 does not comprise a vibration excitation transducer. A vibration excitation transducer may increase the noise recorded by the vibration sensor and needs more energy to be used. Indeed, mechanical waves are naturally generated by the movement of the spinal column. According to one embodiment, the vibration sensor is also able to emit a vibration.

After the implantation of the implantable bone distraction device 1 on the user body, a process of osteogenesis is expected between the two separated bone sections. The advancement of the bone fusion process is able to modify the stiffness of the medium comprising the implantable bone distraction device 1 and the separated bone sections 2, 2' and then, is able to modify the vibration response.

Because of the movement of the human body during a day, the implantable bone distraction device is continuously exposed to vibrations. These vibrations are associated to various frequencies.

By recording continuously or semi-continuously these frequencies with the vibration sensor, the applicant found that, with enough time (from several hours to a few days), a wide range of frequencies were recorded which can allow the medical device to analyze the vibration response on a wide range of frequencies.

In other words, the monitoring of the amplitudes of the vibrations and their frequencies, makes it possible to generate a frequency spectrum of the vibrations in the medium comprising the implantable bone distraction device.

In another embodiment, mechanical vibrations may be generated by a device at the exterior of the human body.

In one embodiment, the implantable bone distraction device 1 further comprises means for transmitting data measured by the vibration sensor from the implantable bone distraction device 1 or from the vibration sensor to an external device.

In one embodiment, the implantable bone distraction device 1 further comprises a wireless interface for transmitting said measurements.

In one embodiment, the implantable bone distraction device 1 further comprises means for storing the data measured by the at least one vibration sensor 6. Said means for storing the measured data may be a memory, said memory being connected to the at least one vibration sensor 6.

In one embodiment, said memory is connected to an interface (which may be wireless) for transmitting said measured data.

In one embodiment, the drive rod actuator 4 is cooperating with the drive rod 5. This cooperation leads to an adjustment (increase or decrease) of the space between the first and second blocks 3, 3', enabling distraction between the first and second bone sections 2, 2'.

Indeed, the distraction process includes increasing the space between the two bone sections when a bridge of bone fusion is achieved. The activation of said drive rod actuator leads to the rotation of the rotatable drive rod and increases the space between the first and second bone sections.

In one embodiment, the detection of a formation of a bridge of bone fusion between the two bone sections automatically activates the actuator to increase the space between the two bone sections.

In one embodiment, the implantable bone distraction device 1 comprises actuation means for actuating the drive rod actuator 4. According to one embodiment, said actuation means for actuating the drive rod actuator 4 are connected to an external device. According to one embodiment, the drive rod actuator 4 comprises an electric, pneumatic or hydraulic motor able to actuate the drive rod actuator 4.

In a preferred embodiment, said actuation means for actuating the drive rod actuator 4 comprises a receiver. Said receiver may be able to receive a signal from an external device, and to activate the drive rod actuator 4.

According to a second aspect, the present invention relates to a medical monitoring device comprising a receiver and a calculator.

In one embodiment, the medical monitoring device comprises a receiver for receiving data from an implantable bone distraction device corresponding to mechanical vibrations of the medium. In one embodiment, said medium comprises the implantable bone distraction device and optionally further comprises the two separated bone sections and/or the callus between said two separated bone sections.

In one embodiment, the medical monitoring device comprises a calculator for computing, from the received data, a distraction indicator.

In one embodiment, said distraction indicator is computed by the calculator through at least the steps of:
  determining at least one first vibration pattern of said medium from the vibration response measured by the at least one sensor 6;
  analyzing the evolution of a first value of at least one vibration pattern of said medium, determined from the measured vibration response during a first period;
  generating a distraction indicator when the first value exceeds a predefined threshold.

In one embodiment, said distraction indicator is computed by the calculator through at least the steps of:
  determining at least one first vibration pattern of said medium from the vibration response measured by the at least one sensor 6;
  analyzing the evolution of a first value of at least one vibration pattern of said medium, determined from the measured vibration response during a first period; and defining said first value as a reference value;
  overtime, analyzing the evolution of at least one second value of the at least one vibration pattern of said medium, determined from the measured vibration response during a second period;
  comparing the at least one second value and said reference first value;
  generating a distraction indicator when said comparison exceeds a predefined threshold.

In one embodiment, the evolution of values is determined as a function of a comparison between the first value and the at least one second value.

In one embodiment, the predefined threshold is manually provided to the calculator through a user interface. According to one embodiment, said predetermined threshold is ranging from 1% to 7% of the first value, preferably ranging from 0.5% to 10% of the first value or ranging from 0.5% to 20% of the first value.

In one embodiment, the at least one vibration pattern is continuously or semi-continuously determined. In one embodiment, when a first value of said vibration pattern is determined, said first value becomes the reference.

When a second value of said vibration pattern is determined, the calculator compares said new second value to the reference. In one embodiment, the comparison is a difference or a function comprising a difference. In one embodiment, when said difference exceeds a predetermined threshold, the calculator generates a distraction indicator.

According to one embodiment, the step of comparing the first value and the at least one second value comprises steps of calculating the difference between the first value and the second value, and comparing said difference to a predetermined threshold.

According to one embodiment, said predetermined threshold is ranging from 1% to 7% of the first value, preferably ranging from 0.5% to 10% of the first value or ranging from 0.5% to 20% of the first value.

In one embodiment, the calculator repeatedly executes the step of determining a second value of said vibration pattern and comparing said second value to the reference until said comparison exceeds the predefined threshold.

In one embodiment, said distraction indicator indicates a structural change of the physical properties of the callus between the first period and a second period during which the second value is determined.

In one embodiment, said generated distraction indicator reflects a structural change of the medium comprising the callus between two periods of time. In one embodiment, said generated distraction indicator reflects a structural change of the medium comprising the callus between a first period of reference and a second period. In one embodiment, the first period of reference corresponds to the period of the last activation of the drive rod actuator.

In one embodiment, the distraction indicator reflects a beginning of a solidification of the callus.

The operator can then actuate the implantable bone distraction device to adjust the space between the separated bone sections allowing distraction. In one embodiment, the method is executed from the beginning after an adjustment of the space between the separated bone sections. In one embodiment, the first value of the vibration pattern or the reference is the first value of the vibration pattern determined after an adjustment of the space between the separated bone sections.

According to one embodiment, said monitoring device further comprises an impedance meter, and/or a user interface such as a display. According to one embodiment, said interface is required to allow the user to provide measurement parameters and to display the at least one generated distraction indicator.

In one embodiment, the calculator comprises a memory. In one embodiment, said memory comprises a value of a predefined threshold. In one embodiment, the calculator is able to store the determined values of the vibration pattern in its memory. According to one embodiment, the medical monitoring device comprises a memory unit able to store the measured data received from the implantable bone distraction device.

In one embodiment, the computation step comprises the steps of:
  determining at least one second value of the at least one vibration pattern of said medium from the measured vibration response;
  comparing the first value and the at least one second value;
  determining an evolution as a function of said comparison.

In one embodiment, the present invention uses the measure of the vibration response to provide information on the bone fusion process. The measurement of said vibration leads to the observation of some vibration patterns.

In one embodiment, said vibration pattern is the resonant frequency. Generally, when a solid material is exposed to vibrations, the response of said material to said vibrations is substantially the same. However, there are specific frequencies for which the response is relevantly higher than for the other frequencies. These specific frequencies are called resonant frequencies.

According to one embodiment where the vibration pattern is the resonant frequency, the method comprises the step of scanning the vibration response measured for each vibration frequency of the measured spectrum of frequencies. In one embodiment, the method comprises the step of determining at least one resonant frequency of reference for which the vibration response is relevantly higher than for the other frequencies. According to one embodiment, the received data is a spectrum of frequency.

In one embodiment, the step of calculating the at least one resonant frequency value of the medium, comprises steps of:
  from the measurements made by the vibration sensor, scanning for each frequency the vibration response of said medium;
  identifying at least one peak of said vibration response;
  optionally recording the frequency value of the center of said at least one peak;
  optionally labelling said frequency value as the resonant frequency value.

According to another embodiment, another vibration pattern can be used to achieve the same purpose. Said vibration pattern can be a feature of the frequency spectrum. Said vibration pattern can also be the amplitude of the signal at one predetermined frequency or the measured spectrum of frequencies.

According to one embodiment, the medical monitoring device monitors said at least one resonant frequency value to obtain information about the bone fusion process between the two separated bone sections.

In another embodiment, the vibration pattern is the vibration response measured at a predetermined number of frequencies. For example, the vibration pattern can be the vibration response of the medium at sensibly 2000, 2500, 3000, 4000 and/or 4500 Hz. According to one embodiment, said vibration pattern is the amplitude of the signal at at least one predetermined frequency.

According to one embodiment, said vibration pattern is the amplitude of the signal at a predetermined frequency. According to one embodiment, said vibration pattern is a mathematical transform of the vibration response such as a Fourier transform or a wavelet transform. According to one embodiment, said vibration pattern is a variation of the frequency during the time.

According to one embodiment, this invention includes means for calculating a modal damping factor (MDF). Advantageously, in this invention, the frequency spectrum is used to calculate a damping factor which is proportional to the width of the resonant peak about the peak's center frequency.

In one embodiment, the steps carried out by the calculator are iteratively carried out. In one embodiment, the steps carried out by the calculator are carried out in a closed loop method. In one embodiment, the calculator semi-continuously executes these steps to semi-continuously generate a distraction indicator. In one embodiment, the calculator continuously executes these steps to continuously generate a distraction indicator.

According to the present invention, the calculator comprises at least one vibration pattern of reference. According to one embodiment, the medical device comprises a memory unit comprising at least one vibration pattern of reference.

Said computer-readable data carrier determines or calculates at least one vibration pattern of the medium comprising the implantable bone distraction device and the separated bone sections and compares said vibration pattern with a vibration pattern of reference. From said comparison, the computer comprising said computer-readable data carrier is able to determine if the gap between the two bone sections should be increased or not and optionally, to transmit to the actuator, a command to increase this gap.

According to one embodiment, said medical monitoring device is configured to be placed outside the body of the user. According to one embodiment, said medical monitoring device is a belt, preferably an abdominal belt.

In one embodiment, numerical or analogical amplifiers or filters may be used in order to treat the vibration signals before extracting a vibration pattern. A correlation method, for instance using maximum likelihood criteria, may be applied with some predefined signals having some predefined patterns in order to extract some vibration patterns of the measured signal.

From the measurement of the vibration response, a computer connected to the computer-readable data carrier is able to calculate the at least one vibration pattern of the medium and any other suitable information from the recorded data.

A third aspect of the present invention relates to a medical system comprising an implantable bone distraction device 1 according to the first aspect of the present invention and a medical monitoring device according to the second aspect of the present invention. In one embodiment, said medical device comprises an interface which activates the transmission of vibration data from the implantable bone distraction device 1 to be received by the medical monitoring device.

In one embodiment, the medical system comprises communication means to connect the implantable bone distraction device 1 and the medical monitoring device. In one embodiment, said communication means comprises wireless transmission means. The transmission means may comprise at least one transmitter and at least one receiver. In one embodiment, the implantable bone distraction device 1 and the medical monitoring device both comprise means for transmitting said measurements. In one embodiment, the medical system comprises means for transmitting said measurements and said means allow a bi-directional communication between the medical monitoring device and the implantable bone distraction device 1, or between the medical monitoring device and the vibration sensor 6.

Data collected by the at least one vibration sensor 6 are then transmitted to the medical monitoring device. The medical monitoring device is then able to process these data as explained below in order to generate a distraction indicator when the evolution of the vibration pattern exceeds a predefined threshold.

According to one embodiment, the medical monitoring device comprises means to provide energy. According to one embodiment, the medical monitoring device can provide the energy to be supplied to the implantable bone distraction device 1. According to one embodiment, the medical monitoring device comprises wireless power transferring means to supply energy to the implantable bone distraction device 1. According to one embodiment, the medical monitoring device comprises a wireless transmitter connected to a power source.

According to one embodiment, the implantable bone distraction device 1 comprises at least one receiver. According to another embodiment, the medical system comprises a receiver connected with wire to the implantable bone distraction device. According to one embodiment, the wireless transmitter connected to a power source conveys the field energy across an intervening space to said receiver, and said receiver converts back said field energy to an electrical current.

In said embodiment, the medical system is able to provide energy to the wireless interface for transmitting measurements and/or to the vibration sensor and optionally to the drive rod actuator.

In one preferred embodiment, the implantable bone distraction device comprises at least a receiver for receiving energy and at least one transmitter for sending the measurement data to the medical monitoring device. According to said embodiment, the receiver is electrically connected to the means for transmitting data and to the drive rod actuator.

According to one embodiment, which is not illustrated, the implantable bone distraction device is connected to said receiver for receiving energy and connected to said at least one transmitter for sending the measurement data to the medical monitoring device by a wire.

According to a fourth aspect, the present invention relates to a medical device for distracting osteotomically separated bone sections, comprising an implantable bone distraction device 1 according to the first aspect of the present invention and a computer-readable data carrier. In one embodiment, said medical device further comprises means for transmitting said measurements from the implantable bone distraction device 1 to the computer-readable data carrier. In one embodiment, said computer-readable data carrier comprises:
at least one threshold value; and
instructions which, when executed by a computer, cause the computer to carry out the step of:
  a. determining at least one first vibration pattern of the medium from the measured vibration response; and
  b. overtime, determining at least one second vibration pattern of said medium from the measured vibration response;
  c. calculating a difference between the at least one first vibration pattern and the at least one second vibration pattern;
  d. generating a distraction indicator when the value of said calculated difference exceeds the at least one threshold value.

In one embodiment, if the calculated difference does not exceed the at least one threshold value, the computer carries out come-back to the step b.

In one embodiment, the steps a), b), c) and d) are iteratively executed.

In one embodiment, if the calculated difference exceeds the at least one threshold value, the instructions further comprise a step of automatically and remotely activating the actuator.

In one embodiment, said computer-readable data carrier further comprises instructions of automatically activating the actuator or the drive rod actuator 4 when a distraction indicator is generated.

In one embodiment, the device comprises means for distracting. In one embodiment, means for distracting provide a distraction between the two separated bone sections.

In one embodiment, the distraction is actuated on the base of the measured vibration response.

In one embodiment, the means for distracting comprise a transmitter to transmit a measured vibration response to the actuator. In one embodiment, when the calculator of the medical monitoring device generates a distraction indicator, the transmitter sends a signal to the actuator. In one embodiment, the transmitter remotely activates the actuator providing a distraction of the separated bone sections.

In one embodiment, the drive rod actuator 4 is automatically activated when a distraction indicator is generated.

In one embodiment, the remote activation of the drive rod actuator leads to adjust the space between two separated bone sections by increasing or reducing said space of a predetermined pitch.

According to a fifth aspect, the present invention relates to a method. According to one embodiment, said method is a monitoring method. In one embodiment, said method comprises steps of:
receiving data from an implantable bone distraction device 1, corresponding to a mechanical vibration response of a medium;
computing from the received data a distraction indicator by:
  determining at least one vibration pattern of said medium from the measured vibration response;

analyzing the evolution of a first value of the at least one vibration pattern from the vibration response measured during a first period; and generating a distraction indicator when the first value exceeds a predefined threshold.

In one embodiment, said method is a closed loop method. In one embodiment, the present method comprises iteratively the steps of receiving and computing. In one embodiment, the method semi-continuously executes these steps to semi-continuously generate a distraction indicator. In one embodiment, the method continuously executes these steps to continuously generate a distraction indicator.

In one embodiment, said method further comprises the step of activating the actuator when a distraction indicator is generated.

In one embodiment, said method is an opened loop method.

The present invention further relates to an operating method comprising the monitoring method according to the present invention and a step of adjusting the space between two separated bone sections by increasing or reducing said space of a predetermined pitch when the distraction indicator is generated.

In one embodiment, a predetermined pitch is a distance which could be applied to move apart two separated bone sections without breaking the callus between said two separated bone sections. In one embodiment, said pitch is ranging from 0.1 to 5 mm.

In one embodiment, said method uses the medical system according to the third aspect of the present invention.

While various embodiments have been described and illustrated, the detailed description is not to be construed as being limited hereto. Various modifications can be made to the embodiments by those skilled in the art without departing from the true spirit and scope of the disclosure as defined by the claims.

REFERENCES

1—Implantable bone distraction device
2—First bone section
2'—Second bone section
3—First block
3'—Second block
4—Drive rod actuator
5—Drive rod
6—Vibration sensor

The invention claimed is:

1. An implantable bone distraction device for distracting osteotomically separated bone sections, said implantable distraction device comprising:
   a first block for implantation and attachment to a first bone section, said first block defining a first chamber bore;
   a second block for implantation and attachment to a second bone section separated from the first bone section by an osteotomy, said second block defining a second chamber bore;
   an actuator including means for adjusting the space between the first block and the second block when activated, enabling distraction between the first bone section and the second bone section;
   at least one vibration sensor arranged in an area located between the first block and the second block and oriented in order to measure a vibration response of a medium comprising the implantable bone distraction device.

2. The implantable bone distraction device according to claim 1, wherein the at least one vibration sensor is a piezoelectric element or an accelerometer.

3. The implantable bone distraction device according to claim 1, wherein the at least one vibration sensor is arranged to measure a vibration response corresponding to mechanical vibrations.

4. The implantable bone distraction device according to claim 1, wherein the medium further comprises the first bone section and the second bone section.

5. The implantable bone distraction device according to claim 1, wherein the at least one vibration sensor is arranged to measure an evolution of the vibration response of the medium, allowing monitoring of an evolution of a bone fusion process.

6. The implantable bone distraction device of claim 5, wherein the evolution of the vibration response is an indicator of callus formation between the first bone section and the second bone section.

7. The implantable bone distraction device according to claim 1, further comprising a drive rod having a first end received in said first chamber bore and a second end, opposite from said first end, received in said second chamber bore; said drive rod being able to adjust the space between the first block and the second block; wherein
   the first chamber bore is a drive chamber bore;
   the second chamber bore is a threaded bore;
   the second end of the drive rod is a threaded end threadably received in the threaded bore of the second block; and further wherein
   the actuator cooperates with said drive rod to rotate said drive rod; said drive rod being able to adjust the space between the first block and the second block by rotation.

8. The implantable bone distraction device according to claim 1, wherein said implantable bone distraction device does not comprise a vibration excitation transducer.

9. The implantable bone distraction device of claim 1, further comprising:
   a receiver for receiving the vibration data from the at least one vibration sensor; and
   a calculator for calculating a distraction indicator from the received vibration data as a function of an evolution of the vibration data over time, wherein the evolution of the vibration data is an indicator of callus formation between the first bone section and the second bone section.

10. The implantable bone distraction device of claim 9, wherein calculating the distraction indicator from the received vibration data comprises steps of:
    determining at least one vibration pattern of said medium from the vibration response measured by the at least one vibration sensor;
    analyzing an evolution of a first value of the at least one vibration pattern of said medium determined from the measured vibration response during a first period;
    analyzing an evolution of a second value of the at least one vibration pattern of said medium determined from the measured vibration response during a second period;
    performing a comparison between the first value and the second value; and
    generating a distraction indicator as a function of said comparison.

11. A medical monitoring device comprising:
    a receiver for receiving data from an implantable bone distraction device implanted and attached between two bone sections of the same bone, corresponding to a mechanical vibration response of a medium comprising the implantable bone distraction device, as measured by at least one vibration sensor;

a calculator for computing, from the data received by the receiver, a distraction indicator through at least the steps of:
- determining at least one vibration pattern of said medium from the mechanical vibration response measured by the at least one vibration sensor;
- analyzing an evolution of a first value of the at least one vibration pattern of said medium determined from the measured vibration response during a first period;
- analyzing an evolution of a second value of the at least one vibration pattern of said medium determined from the measured vibration response during a second period;
- performing a comparison between the first value and the second value; and
- generating the distraction indicator as a function of the comparison.

12. The medical monitoring device according to claim 11, wherein the calculator performs the step of generating the distraction indicator when the first value exceeds a predefined threshold.

13. The medical monitoring device according to claim 11, wherein the calculator performs the step of generating a distraction indicator when said comparison exceeds a predefined threshold.

14. The medical monitoring device according to claim 13, wherein the at least one vibration pattern is a function of a dampening factor, wherein the predefined threshold is equal to approximately 0.5 percent to approximately 20 percent of the first value, and wherein the calculator repeatedly determines the second value of the at least one vibration pattern of the medium and compares the first value and the second value until the second value exceeds the predefined threshold.

15. The medical monitoring device according to claim 11, further comprising a transmitter for transmitting to the implantable bone distraction device instructions for providing a distraction when the distraction indicator is generated by the calculator.

16. The medical monitoring device according to claim 11, wherein the mechanical vibration response of the medium measured by the at least one vibration sensor allows monitoring of an evolution of a bone fusion process.

17. A medical system comprising:
- an implantable bone distraction device according to claim 1;
- a medical monitoring device according to claim 10; and
- an interface which activates the transmission of vibration data from the implantable bone distraction device, to be received by the medical monitoring device, wherein the vibration data correspond to a mechanical vibration response of a medium comprising the implantable bone distraction device, as measured by at least one vibration sensor.

18. The medical system according to claim 17, wherein the implantable bone distraction device comprises actuation means for actuating the actuator; and wherein the medical monitoring device comprises a transmitter connected to said actuation means for automatically activating the actuator when a distraction indicator is generated.

* * * * *